(12) United States Patent
Lu et al.

(10) Patent No.: US 9,797,862 B2
(45) Date of Patent: Oct. 24, 2017

(54) DIELECTROPHORESIS-BASED CELL DESTRUCTION TO ELIMINATE UNWANTED SUBPOPULATIONS OF CELLS

(71) Applicant: THE REGENTS OF THE UNIVERSITY OF CALIFORNIA, Oakland, CA (US)

(72) Inventors: Jente Lu, Irvine, CA (US); Lisa A. Flanagan, Irvine, CA (US); Abraham P. Lee, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 585 days.

(21) Appl. No.: 14/318,386

(22) Filed: Jun. 27, 2014

(65) Prior Publication Data

US 2015/0001081 A1    Jan. 1, 2015

Related U.S. Application Data

(60) Provisional application No. 61/841,063, filed on Jun. 28, 2013.

(51) Int. Cl.
| | |
|---|---|
| G01N 27/44 | (2006.01) |
| G01N 27/447 | (2006.01) |
| B03C 5/00 | (2006.01) |
| B03C 5/02 | (2006.01) |
| B01L 3/00 | (2006.01) |

(52) U.S. Cl.
CPC .. G01N 27/44782 (2013.01); B01L 3/502761 (2013.01); B03C 5/005 (2013.01); B03C 5/026 (2013.01); *B01L 2200/0668* (2013.01); *B01L 2300/0816* (2013.01); *B01L 2300/0819* (2013.01); *B01L 2300/0877* (2013.01); *B01L 2400/0409* (2013.01); *B01L 2400/0424* (2013.01); *B03C 2201/26* (2013.01)

(58) Field of Classification Search
CPC ..... B01L 2300/0645; B01L 2400/0424; G01N 2015/149; G01N 27/44782
See application file for complete search history.

(56) References Cited

PUBLICATIONS

Prieto et al. Lab Chip, 2012, 12, 2182-2189.*
Gascoyne et al. IEEE Trans Ind Appl. 1997; 33(3):670-678.*
Wang et al. J. Phys. D: Appl. Phys. 26 (1993) 1278-1285.*
(Continued)

*Primary Examiner* — Sally Merkling
(74) *Attorney, Agent, or Firm* — Vista IP Law Group LLP

(57) ABSTRACT

A method for enriching a heterogeneous population of cells includes loading one or more sample chambers containing DEP electrodes therein with a solution containing the heterogeneous population of cells, wherein the heterogeneous population of cells comprises a first subpopulation of cells having a first crossover frequency and a second subpopulation of cells having a second, higher crossover frequency. An AC electrical field is applied to the DEP electrodes, wherein the AC electrical field has an applied frequency that is between the crossover frequency of the first subpopulation of cells and the second subpopulation of cells, wherein the first subpopulation of cells are substantially killed by the applied electrical field and the second subpopulation of cells are substantially not killed by the applied electrical field.

15 Claims, 6 Drawing Sheets

(56) References Cited

PUBLICATIONS

Labeed, Fatima H. et al., Biophysical Characteristics Reveal Neural Stem Cell Differentiation Potential, PLoS ONE, www.plosone.org, Sep. 2011, vol. 6, Issue 9, e25458 (11pages).

Lu, Jente et al., Advancing practical usage of microtechnology: a study of the functional consequences of dielectrophoresis on neural stem, Integr Biol (Camb). Oct. 2012; 4(10):. doi:10.1039/c2ib20171b (29pages).

Gascoyne, Peter R.C. et al., Dielectrophoretic Separation of Cancer Cells from Blood, IEEE Trans Ind Appl. 1997; 33(3): 670-678; doi:10.1109/28.585856.

Nourse, J.L. et al., Membrane Biophysics Define Neuron and Astrocyte Progenitors in the Neural Lineage, Stem Cells 2014; 32:706-716 www.stemcells.com.

Prieto, Javier L. et al., Frequency discretization in dielectrophoretic assisted cell sorting arrays to isolate neural cells, Lab Chip, 2012, 12, 2182-2189.

* cited by examiner

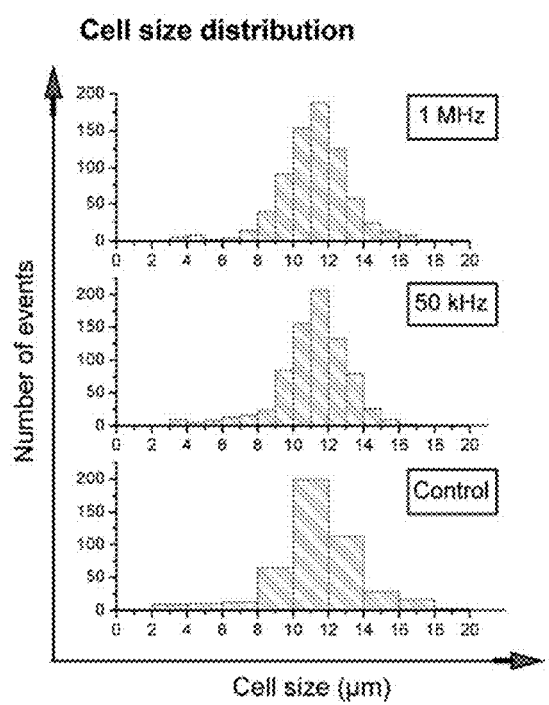
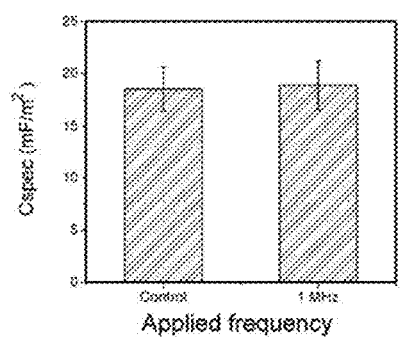
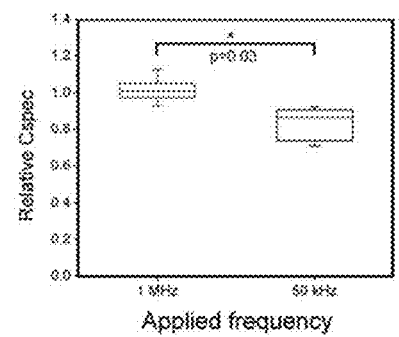
FIG. 6A
FIG. 6B
FIG. 6C

DIELECTROPHORESIS-BASED CELL DESTRUCTION TO ELIMINATE UNWANTED SUBPOPULATIONS OF CELLS

RELATED APPLICATION

This Application claims priority to U.S. Provisional Patent Application No. 61/841,063 filed on Jun. 28, 2013, which is hereby incorporated by reference in its entirety. Priority is claimed pursuant to 35 U.S.C. §119.

STATEMENT REGARDING FEDERALLY SPONSORED RESEARCH AND DEVELOPMENT

This invention was made with Government support under Grant No. AG023583, awarded by the National Institutes of Health. The Government has certain rights in this invention.

FIELD OF THE INVENTION

The field of the invention generally relates to dielectrophoresis-based ("DEP-based") devices and methods. DEP is the force created on a neutral particle like a cell due to the interaction of a particle's induced dipole and the spatial gradient of a non-uniform AC electric field. More particularly, the field of the invention relates to DEP-based devices and methods used to enrich and/or remove a subpopulation of cells without the need for labeling the cells in advance. The methods and devices may also be useful as a tool for the high-throughput cell enrichment without using cell surface markers. The tool may also be used as a research and investigative tool that is able to discover specific cell markers to advance the field.

BACKGROUND

Previously, fluorescence activated cell sorting (FACS) has been the standard way to isolate subpopulations of cells, particularly in the field of hematopoietic stem cells. However, FACS has been limited for use in many cases in which there are not specific markers for the cells of interest, such as isolating neuronal progenitors or astrocytic progenitors from neural stem/progenitor cells due to the unavailability of specific cell surface markers for the subpopulations of cells. FACS devices are, however, very expensive and occupy a large amount of space in the laboratory. FACS devices require expensive and complicated lasers in addition to requiring labels and antibodies to perform the FACS analysis.

DEP has been used to separate certain types of cells in solution. For example, Gascoyne et al. demonstrated the DEP separation of MDA-231 human breast cancer cells from blood. Gascoyne et al., Dielectrophoretic Separation of Cancer Cells from Blood, IEEE Trans Ind Appl., Vol. 33, pp. 670-78 (1997). DEP has also been used to sort neurons from a heterogeneous population of mouse-derived neural stem and progenitor cells (NSPCs) and neurons. See Prieto et al., Frequency discretization in dielectrophoretic assisted cell sorting arrays to isolation neural cells, Lab Chip, 12, pp. 2182-89 (2012). DEP has also been used in the sorting of neuron progenitors and astrocyte progenitors form NSPCs. See Nourse et al., Membrane Biophysics Define Neuron and Astrocyte Progenitors in the Neural Lineage, Stem Cells, 32, 706-16 (2014). NSPCs are heterogeneous populations of self-renewing stem cells and more committed progenitors that differentiate into neurons, astrocytes and oligodendrocytes. Due to the present lack of cell surface markers in the field, there are no universal strategies to enrich neuronal progenitors by removing astrocytic progenitors. There is a need for such a solution, including one that does not rely on any particular cell surface marker.

SUMMARY

In one embodiment, with the process described herein, enriching a subpopulation of cells is accomplished by destroying another subpopulation of cells without the need of specific cell surface marker. For example, neurons/neuronal progenitors and neural stem cells are enriched by destroying astrocytic progenitors selectively without markers. This process can expedite the discovery and identification of new cell surface markers to recognize specific subpopulations of cells. For example, by removing targeted subpopulations of cells from a cell mixture, the non-targeted cells become enriched and could be used in analyses of cell surface protein expression. Proteins expressed specifically on the enriched cells would be used to develop cell type specific markers. This strategy is applicable to any cell mixture, including those that contain stem cells or cancer cells. Moreover, the method could be extensively used for any naturally formed heterogeneous cell population that has distinct dielectric properties/membrane capacitance so that selective destruction could be used to remove any unwanted cell type in a mixture of cell populations. The method is also not limited to cells derived from any particular species, because the phenomenon has been observed with human and mouse cells.

In another embodiment, a method for enriching a population of cells includes loading one or more sample chambers containing DEP electrodes therein with a solution containing the heterogeneous population of cells, wherein the heterogeneous population of cells comprises a first subpopulation of cells having a first crossover frequency and a second subpopulation of cells having a second, higher crossover frequency. An AC electrical field is applied to the DEP electrodes, wherein the AC electrical field has an applied frequency that is between the crossover frequency of the first subpopulation of cells and the second subpopulation of cells, wherein the first subpopulation of cells are substantially killed by the applied electrical field and the second subpopulation of cells are substantially not killed by the applied electrical field.

In still another embodiment, a system for enriching a heterogeneous population of cells includes at least one sample chamber containing therein interdigitated DEP electrodes on a surface thereof and a function generator operatively coupled to the interdigitated DEP electrodes and configured to apply an AC electrical field to the interdigitated DEP electrodes. The system may also include a centrifugation device which is used to harvest cells that were not killed during activation of the DEP electrodes.

BRIEF DESCRIPTION OF THE DRAWINGS

FIG. 6A illustrates a graph of cell size distribution of huNSPCs SC23 prior to and post DEP exposure.

FIG. 6B illustrates a graph of applied frequency as a function of $C_{spec}$ for huNSPCs exposed to positive DEP (1 MHz) for 30 minutes. AC electric field exposure did not alter the intrinsic electrophysiological properties of the cells.

FIG. 6C illustrates a graph of applied frequency as a function of relative $C_{spec}$ for huNSPCs exposed to DEP (50 kHz). DEP-induced cell destruction leads to the decrease in the population membrane capacitance. A significant decrease in membrane capacitance of the population of huNSPCs SC23 was found between control (no DEP exposure) and cells post-DEP exposure at 50 kHz.

DETAILED DESCRIPTION OF THE ILLUSTRATED EMBODIMENTS

Figure 1:
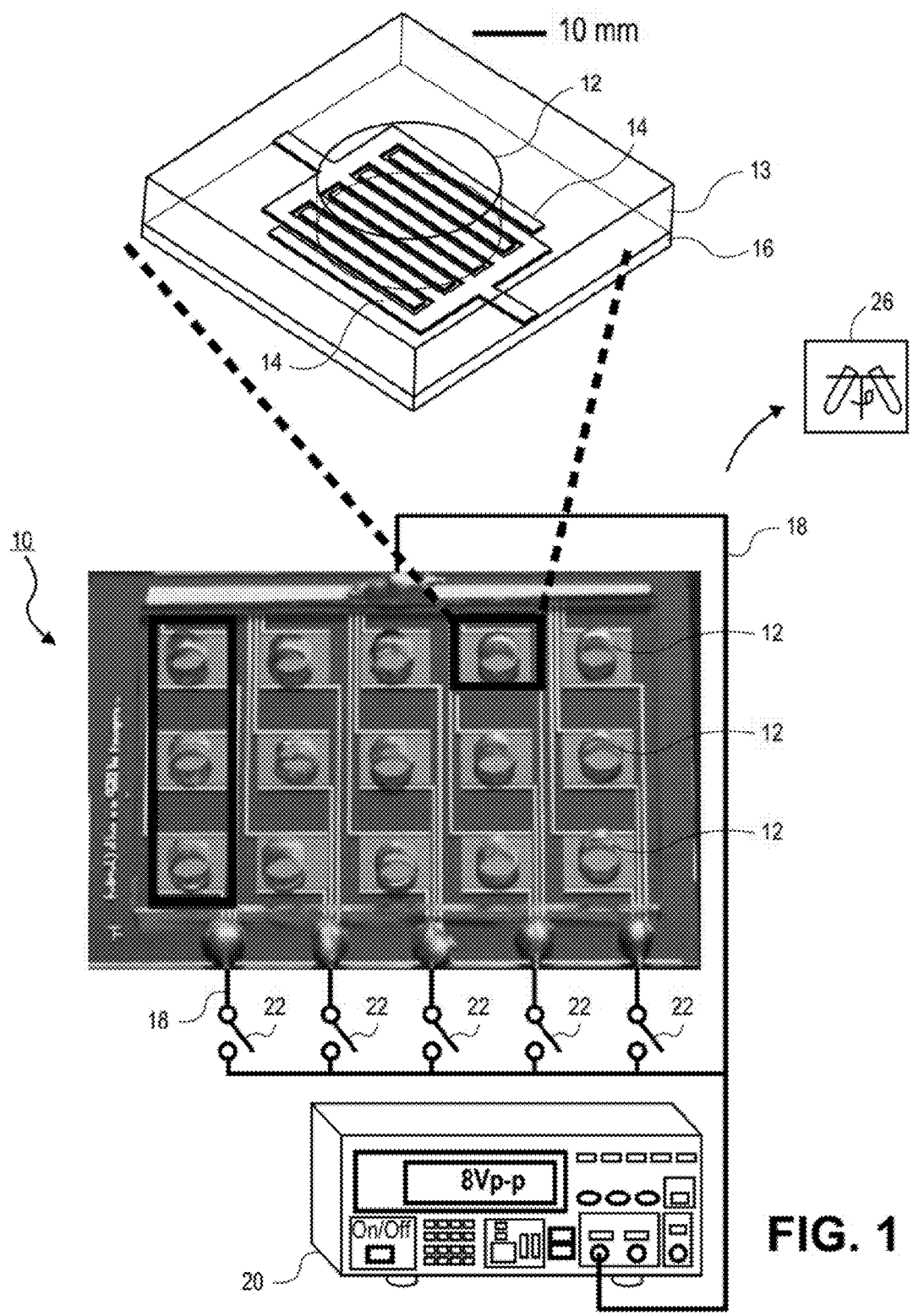
FIG. 1 illustrates a system 10 for enriching a heterogeneous population of cells according to one embodiment.

FIG. 1 illustrates a system 10 for enriching a heterogeneous population of cells according to one embodiment. The system 10 includes at least one sample chamber 12 that contains therein DEP electrodes 14 on a surface within the sample chamber 12. Typically, the DEP electrodes 14 are interdigitated with one another as illustrated in FIG. 1. The DEP electrodes 14 may be deposited on a substrate 16. DEP electrodes 14 may be formed from an electrically conductive metal such as gold or the like. The substrate 16 is typically an electrically non-conductive material such as glass although a polymer material may also be used.

The sample chamber(s) 12 may be formed in layer 13 disposed atop the substrate 16, for example, in the form of a well. In other embodiments, there can be many sample chambers 12, for instance, an array of wells with each well containing the DEP electrodes 14. The sample chamber 12 may also be a flow cell or channel whereby fluid flows over the DEP electrodes 14 located at the bottom thereof. In this regard, the system 10 can be used in both a batch mode as well as a continuous mode.

When the sample chamber 12 is in the form of a well, the DEP electrodes 14 are typically located on a lower surface of the well with the sides rising above the lower surface. The dimensions of the sample chamber 12 may vary but may be several mm in diameter or width and several mm in height. Preferably, the height of the sample chamber 12 is at least several hundred microns such that, as described below, surviving cells can stay some distance away from the activated DEP electrodes 14 such that they can be later collected or retrieved. For example, the "kill zone" created by the activated DEP electrodes 14 may extend some 150-200 μm above the DEP electrodes 14 so the depth of the sample chamber 12 needs to be at least this tall. Still referring to FIG. 1, the interdigitated DEP electrodes 14 are connected to electrical conductors 18 that are connected to a function generator 20. One or more switches 22 or other switching circuitry may be provided so that DEP electrodes 14 can be turned on/off as needed.

A multi-well construction with DEP electrodes 14 contained therein can be fabricated on glass slides (e.g., substrate 16) using known microfluidic construction methods. Briefly, standard lithography techniques can be used to pattern an interdigitated electrode array (e.g., 200 A° titanium and 1000 A° gold) on the top of a glass slide with 50 mm-wide electrodes, spaced 100 mm apart. Pre-cured PDMS layers with wells in a 3×5 array may be bonded to the glass slides to form the side wells (e.g., form layer 13). Exemplary dimensions of each DEP well, may be, for instance 2 mm in diameter and 3 mm in depth. Electric wires can be used as conductors and connected to the DEP electrodes 14 with conductive epoxy (e.g., MG Chemicals, Toronto, Ontario, Canada).

The function generator 20 applies an AC electric field to the electrically connected DEP electrodes 14. The AC electrode field propagates through the solution and acts on the cells contained in the solution. An example of a function generator 20 that can be used includes, without limitation, the arbitrary function generator AFG320 available from Tektronix, Beaverton, Ore. Typically, the voltage that is applied may have a peak-to-peak voltage of at least 8V although other peak-to-peak voltages may be used (e.g., higher than 3V peak-to-peak). Higher peak-to-peak voltages can be used but there may be increased heating of the solution which affect cell health. The applied frequency is set typically just above the crossover frequency of the cells that are desired to be killed. The AC electric field is applied for a period of time which is typically about a minute to several minutes. Longer voltage applications are needed for larger numbers of cells. For example, if there are relatively few cells, application of voltage for about 30 seconds or even tens of seconds may be sufficient. Larger numbers of cells may require longer times (e.g., 1-5 minutes). Still other applications may require a longer application of voltage (e.g., between 5-30 minutes). Of course, various voltage application times are contemplated herein, even those outside any range set forth herein.

In one aspect, the sample chamber 12 (e.g., well) is deep, on the order of about several hundred micrometers or more in height. In one aspect of the invention, the top of the well is open. The deep exposure well allows a large portion of the volume of solution located above the DEP electrodes 14 to be subject to low or no electric field. This permits cells that are not within the killing zone to escape the DEP-based cell destruction region. In this manner, the system 12 has high throughput such that large numbers of cells can be processed at one time. For example, the number of cells that may be processed in the device may include on the order of 100,000 to 10 million cells at a time.

After the DEP electrodes 14 have been energized for a sufficient period of time to selectively kill a subpopulation of cells, the remaining cells, which are located away from the DEP electrodes, 14 are then collected or otherwise retrieved. The solution containing the living cells may be removed through a pipette or other mechanism commonly known to those skilled in the art. The system 12 may also be integrated into a microfluidic lab-on-chip environment whereby the remaining solution may be transferred using various pumping or transfer methods used in connection with microfluidic devices. The cells may be harvested by using a centrifugation device 26 as is illustrated in FIG. 1.

The method and operation of the system and devices disclosed herein primarily relies on the membrane capacitance values of a population or subpopulation of cells. Thus, measuring or deriving the membrane capacitance of the population or subpopulation is the first step. One can then derive the population level crossover frequency according to the following equation.

$$f_{crossover} \approx \frac{\sigma_{medium}}{\sqrt{2}\,\pi r C_{spec}} \quad \text{Eq. 1}$$

where $f_{crossover}$ is the crossover frequency of the population, $\sigma_{medium}$ is the conductivity of medium the cells are suspended in, r is the average radius of the cells, and $C_{spec}$ is the population level membrane capacitance. Once the crossover frequency is derived or measured, DEP force is applied by tuning the applied frequency below the population level crossover frequency with appropriate voltages (e.g., typically above 3 Volts peak-to-peak) to induce DEP-based selective cell destruction. This will selectively remove the cells with higher membrane capacitance to enrich cells in the population with lower membrane capacitance.

For example, the system 10 and method may be used to selectively kill or destroy a subpopulation of cells based on the cells' crossover frequency. Consider, for example, a heterogeneous population of cells that that has two cell types with differing crossover frequencies; type A cells have a high $C_{spec}$ value while type B cells have a low $C_{spec}$ value. As noted above, the crossover frequency $f_{crossover}$ is a function of, among other things, $C_{spec}$ value. The frequency generator 20 can be tuned to apply a crossover frequency that is between the respective crossover values for the type A and type B cells. In this example, the type A cells would be attracted to the DEP electrodes and killed while the type B cells would be repelled from the DEP electrodes and remain alive. The system 12 and method applies to any heterogeneous population of cells in which different cell types have different crossover frequencies. This may include many different types of subpopulations beyond mere binary populations as described above. Moreover, as explained herein, stem cells are one type of cells that show differences in crossover frequencies. However, other types of cells (e.g., cancerous cells v. healthy cells) may also show differences in crossover frequency and can also be selectively destroyed as described herein. These same principles may also apply to other cells such as bacteria that have cell walls.

Similarly, as seen from Eq. 1 above, the crossover frequency of one type of cell (e.g., subpopulation) may change by using different conductivity media. For instance, if there are two types of cells having similar crossover frequency in one conductivity medium, it is possible to change or alter the conductivity of the medium so that the crossover frequency of these two types of cells shift apart from each other. This might not happen in all instances but in certain situations the differential of crossover frequencies can be increased by changing or altering the conductivity of the media surrounding the cells.

By tuning the applied frequency and voltages, the method and device can be used as a process to enrich cells without cell surface markers by removing cells with certain "specific membrane capacitance", $C_{spec}$. Applications include, but are not limited to, facilitation of the discovery of cell surface markers for any cell, enrichment of specific cell types for animal transplantation studies or cell-based therapeutics, and removal of undesired cell types (such as cells that may cause tumors) for cell-based therapeutics.

Figure 2:
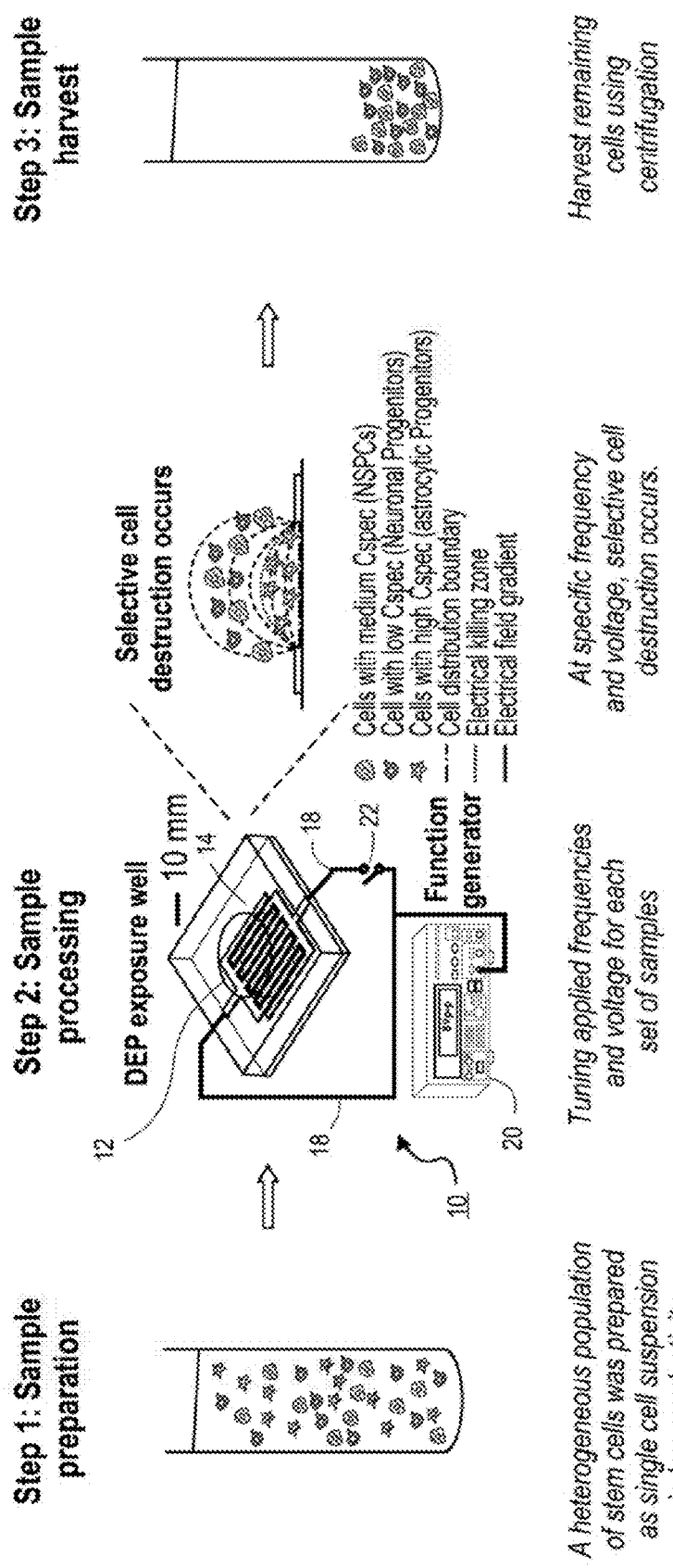
FIG. 2 illustrates a schematic view depicting a method of using DEP-based cell destruction to eliminate and/or remove an unwanted subpopulation of cells.

FIG. 2 illustrates an exemplary method for enriching a heterogeneous population of cells. In this embodiment, as seen in Step 1, a heterogeneous population of cells is prepared as a single cell suspension in a low conductivity DEP buffer (1000/cm). As seen in this particular example, there are cells with medium $C_{spec}$ (NSPCs), cells with low $C_{spec}$ (Neuronal Progenitors), and cells with high $C_{spec}$ (Astrocytic Progenitors). Referring now to Step 2, cells are then loaded into the DEP device 10. The DEP device 10 includes an exposure well 12 (or multiple wells) with each well having interdigitated DEP electrodes 14 located on the bottom thereof. The interdigitated DEP electrodes 14 are connected to a function generator 20 that is configured to apply an AC electrical field to the DEP electrodes 14. At specific frequency and voltages, selective cell destruction occurs. For example, an electrical killing zone is established between adjacent DEP electrodes 14 whereby cells with high $C_{spec}$ (Astrocytic Progenitors) are selectively killed. Cells with medium $C_{spec}$ (NSPCs) and cells with low $C_{spec}$ (Neuronal Progenitors) are outside of the killing zone and are, for example, repelled from the DEP electrodes 14. Referring to Step 3 of FIG. 2, the remaining live cells (e.g., NSPCs and Neuronal Progenitors) are harvested using centrifugation.

Depending on whether the DEP multi-well device is a single-use device or reusable, the device may need sterilization prior to use. Sterilization may include exposure of the device UV light for at least 30 min, followed by washing with 70% EtOH (v/v), milli-Q (Millipore) processed $H_2O$, 0.05% trypsin-EDTA (v/v), and DEP buffer in sequential order in a sterile hood. To use the device, dissociated cell suspensions (100 µL) may be added to each well followed by a 10 min incubation to allow at least 95% of cells to settle to the bottom of the well, allowing consistent proximity to the DEP electrodes 14.

Figure 3A:
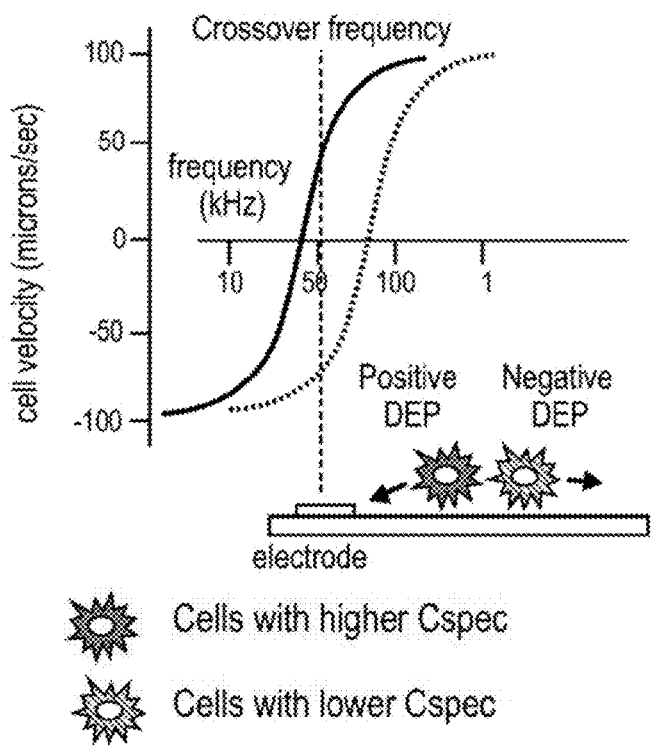
FIG. 3A illustrates, in a heterogeneous cell population, the derived crossover frequency from population level membrane capacitance that represents the average of the crossover frequencies for its subpopulations cells. For the subpopulation with higher $C_{spec}$ (dark cells), applying frequency as the average crossover frequency will result in weak positive DEP forces to attract the cells to high electric field. On the other hand, the applied frequency will induce a negative DEP force to subpopulations of cells with lower $C_{spec}$ (lighter cells) to repel the cells away from high electric field.
Figure 3B:
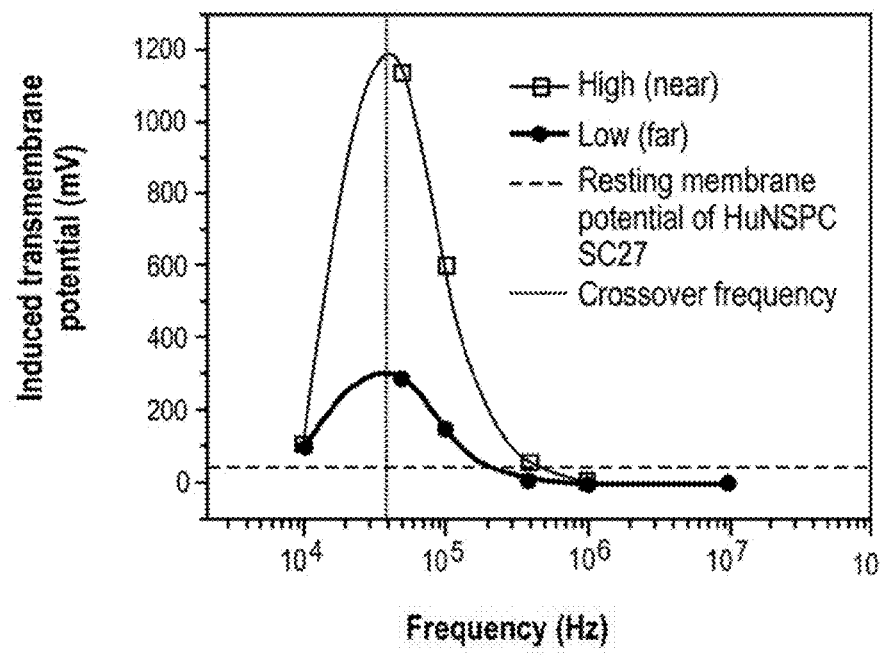
FIG. 3B illustrates results of a computational simulation establishing that DEP-based cell destruction occurs only at frequency slightly above their crossover frequency (vertical line) when induced transmembrane potential is higher than their resting membrane potential (horizontal dashed line) combining the cell's response to DEP force and induced transmembrane potential cause by AC electric field.
Figure 3C:
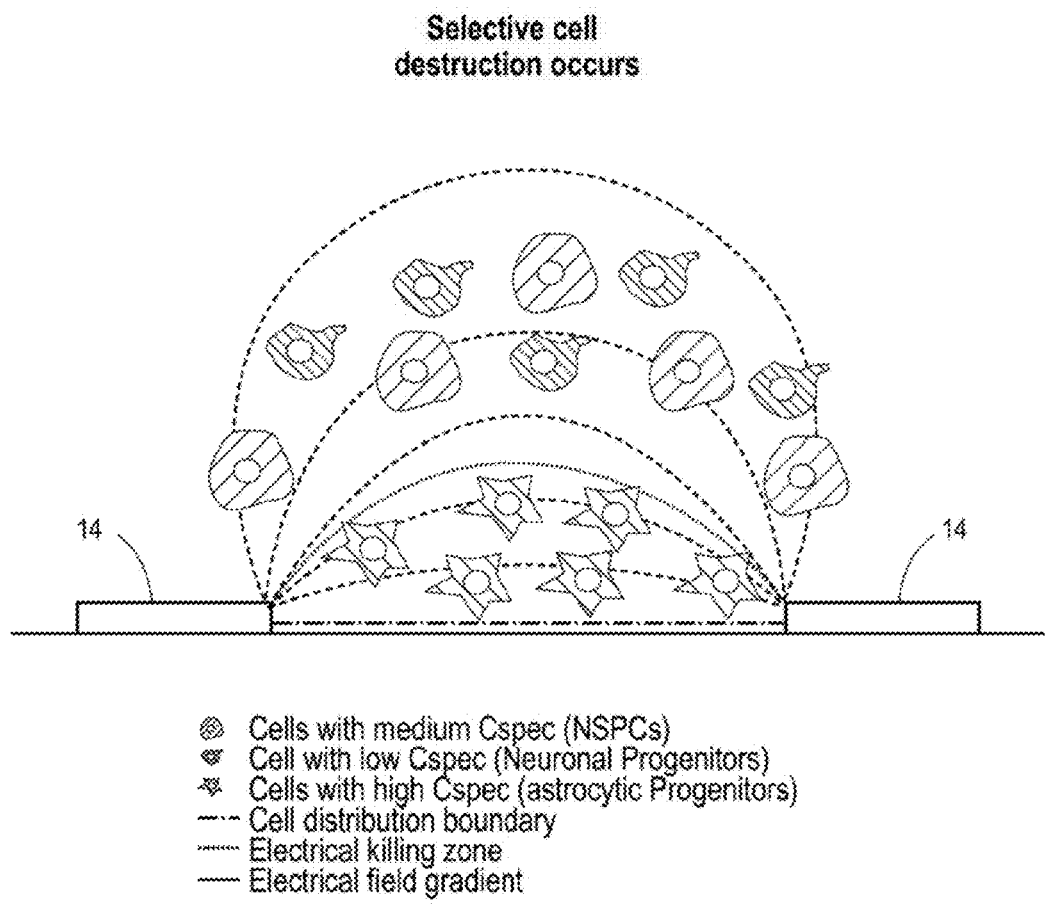
FIG. 3C is a schematic representation showing that cells with higher $C_{spec}$ will be destroyed due to the high electric field exposure while the rest of cells avoided this exposure since they were repelled from the high electric field.

FIGS. 3A-3C illustrate the fundamental aspects of selective DEP-based cell destruction. FIG. 3A illustrates, in a heterogeneous cell population, the derived crossover frequency from population level membrane capacitance that represents the average of the crossover frequencies for its subpopulations of cells. For the subpopulation with higher $C_{spec}$ (dark cells), applying frequency at the average crossover frequency (here 50 kHz) will result in weak positive DEP forces to attract the cells to high electric fields. Conversely, the applied frequency will induce a negative DEP force to subpopulations of cells with lower $C_{spec}$ (lighter cells) to repel the cells away from high electric fields. FIG. 2B illustrates the results of a computational simulation establishing that DEP-based cell destruction occurs only at frequencies slightly above their crossover frequency (vertical line) when induced transmembrane potential is higher than their resting membrane potential (horizontal dashed line) combining the cell's response to DEP force and induced transmembrane potential cause by AC electric field (equation 1). FIG. 3C is a schematic representation showing adjacent DEP electrodes 14 with cells with higher $C_{spec}$ (and are located within the killing zone) that will be destroyed due to the high electric field exposure while the rest of cells are repelled from exposure to the high electric field. Notably, the process of destroying cells does not require markers or other means to identify cells prior to destroying the unwanted subpopulation. The DEP-based cell destruction relies mainly on the intrinsic dielectric properties of the cells, particularly membrane capacitance, which enables unbiased and label free selective cell destruction.

Experimental

In this experiment, DEP-based, label-free cell destruction was used to reduce the heterogeneity of human NSPCs (huNSPCs) by selectively eliminating astrocytic progenitors in culture. A frequency- and exposure duration-dependent relationship was found to exist between the percentage of huNSPCs destroyed by DEP and the number of astrocytes produced. It was confirmed that as more and more astrocytes (GFAP+/Sox2) and astrocytic progenitors (GFAP+/Sox2+) appeared in the culture, more and more cells would be damaged by DEP at 50 kHz for 30 minutes. A subpopulation of cells with higher membrane capacitance in huNSPCs (astrocytic progenitors) were the targets of the DEP-induced cell destruction.

Materials and Methods

Cell Culture

Fetal-derived human NSPC cultures (HuNSPC SC23) isolated from the cerebral cortices at the gestational age of 23 weeks were used. Briefly, undifferentiated cells were grown as adherent cultures on fibronectin coated flasks in basal medium [DMEM/F12 (Invitrogen, Carlsbad, Calif.), 20% (v/v) BIT-9500 (Stem Cell Technologies, Vancouver BC), 1% (v/v) antibiotic/antimycotic (Invitrogen, Carlsbad, Calif.)] supplemented with the following mitogenic growth factors: 40 ng/ml EGF (BD Biosciences, Bedford, Mass.), 40 ng/ml FGF (BD Biosciences, Bedford, Mass.), and 40 ng/ml PDGF (Peprotech, Rocky Hill, N.J.). HuNSPCs were passaged approximately every 7 days using Cell Dissociation Buffer (Invitrogen, Carlsbad, Calif.) and split 1:2. To determine the neuronal and astrocytic fates of huNSPCs, the percentage of NSPCs fated to the neuronal lineage was determined by differentiation of cells for 2 weeks on laminin coated coverslips in differentiation media [1:1 basal medium and Neurobasal medium (Invitrogen, Carlsbad, Calif.) supplemented with B27 (Invitrogen, Carlsbad, Calif.), 1% heat inactivated fetal bovine serum (Invitrogen, Carlsbad, Calif.), 20 ng/ml BDNF (Peprotech, Rocky Hill, N.J.), 20 ng/ml NT3 (Peprotech, Rocky Hill, N.J.), 2.5 ng/ml FGF (BD Biosciences, Bedford, Mass.), and 0.1 uM retinoic acid (Sigma, St. Louis, Mo.)] while the astrocytic culture was induced to differentiate on laminin coated coverslips in DMEM-F12 with 20% FBS for 7, 14, and 21 days with medium changes every other day. All experiments utilized HuNSPCs cultures at passages 8-15. All cell cultures were maintained in a humidified incubator, operating at 37° C. with 5% $CO_2$, until the time of experimentation.

Immunocytochemistry

Immunocytochemistry was performed to determine the fate of the culture, and the following antibodies were used: anti-Sox2 (Y-17) polyclonal, 1:100 (Santa Cruz Biotechnology, Santa Cruz, Calif.); anti-Nestin polyclonal, 1:100 (Chemicon, Temecula, Calif.); anti-GFAP (clone GSA) monoclonal, 1:200 (Sigma, St. Louis, Mo.); anti-MAP2 (microtubule-associated protein 2) (HM2) monoclonal, 1:100 (Sigma, St. Louis, Mo.); anti-glial fibrillary acidic protein (anti-GFAP, clone GSA) monoclonal, 1:200 (Sigma, St. Louis, Mo.). The secondary antibodies were donkey anti-mouse Alexa Fluor 555 and donkey anti-goat/rabbit Alexa Fluor 488, dilution of 1:100 (Molecular Probes/Invitrogen, Carlsbad, Calif.). Neurons were Map2-positive cells with neuritis at least 3× length of cell body for HuNSPCs. Astrocytes were GFAP-positive and Sox2-negative cells, which distinguished them from GFAP-expressing NSPCs. At least 1000 cells were counted for each experimental condition from images of five randomly selected fields. The CellProfiler, an open-source software (Broad Institute, Cambridge, Mass., www.cellprofiler.org), was used to determine % of astrocyte (GFAP+/Sox2−) cells in addition to the nuclei count. The double-blind method was used to manually quantify Map2+ cells for each condition.

Cell Preparation for DEP

HuNSPCs were dissociated into a single cell suspension for DEP experiments using Cell Dissociation Buffer (Invitrogen, Carlsbad, Calif.) while 0.5% trypsin EDTA (Invitrogen, Carlsbad, Calif.) was used to dissociate astrocytic cultures. Dissociated cells were washed once with and resuspended into DEP buffer, an iso-osmotic medium consisting of 8.5% (w/v) sucrose, 0.3% (w/v) glucose, adjusted to a final conductivity of 110 µS/cm using RPMI-1640 medium for DEP exposure, but 100 µS/cm using KCl for the measurement of their dielectric properties using DEP dot microsystem. The conductivity was measured with a conductivity meter (Thermo Orion, Beverly, Mass.). The final cell concentration was adjusted to $1 \times 10^6$ cells/mL for all DEP-exposure experiments, but $6 \times 10^6$ cells/mL for dielectric properties.

DEP Well Device Fabrication

Standard lithography techniques were used to pattern an interdigitated electrode array (200 Å titanium and 1000 Å gold) on the top of the glass slide with 50 µm-wide electrodes, spaced 100 µm apart. Pre-cured PDMS layers with wells in a 3×5 array were bonded to the glass slides to form the wells. The dimensions of each DEP well are 0.2 cm in diameter and 3 mm in depth. Electric wires were connected to the device electrodes with conductive epoxy (MG Chemicals, Toronto, Ontario, Canada).

DEP Exposure

Prior to DEP exposure experiments, the DEP well device was sterilized by UV light for at least 30 min, followed by washings with 70% EtOH (v/v), mQ $H_2O$, 0.05% trypsin-EDTA (v/v), and DEP buffer in sequential order in sterile conditions. DEP exposure experiments were performed in the tissue culture hood to maintain sterility of the cells. Single-cell suspensions (100 µl) were added to each well followed by a 10-min incubation to allow at least 95% of cells to settle to the bottom of the well, allowing consistent proximity to electrodes. An AC electric field was applied to the cells using function generator AFG320 (Tektronic, Beavrton, Ore.) with 8V peak to peak for testing frequencies of 10 kHz, 50 kHz, 100 kHz, and 1 MHz and DEP exposure times of 1, 5, 10, and 30 min. Post-DEP exposure analysis was performed at the end of each run to evaluate the influence of DEP on cells.

Survival Analysis

The effect of DEP exposure on viability and cell membrane integrity was assessed by calculating the percentage of cells excluding trypan blue using a hemacytometer. The viability data will be normalized to the control to derived the cell survival post-DEP exposure as shown below:

$$\% \text{ Cell survival} = \left(\frac{Viability_{DEP}}{viability_{control}}\right) \times 100\% \quad \text{Eq. 2}$$

where the subscript DEP and control represent cells with and without DEP exposure. All survival analyses were performed in at least three independent experiments for each condition.

Electrophysiological Properties and Diameter Profile Measurement

DEP measurements were obtained using the DEP system as described in Fatoyinbo et al., "Rapid-on-chip determination of dielectric properties of biological cells using imaging techniques in a dielectrophoresis dot microsystem." ELECTROPHORESIS, 29: 3-10 (2008) which is incorporated by reference herein. Cells were placed in wells with dimensions similar to those in a 1536-well plate, but bearing 12 ring-shaped, 17 mm-wide, gold-plated copper electrodes around the well circumference with gaps of 75 mm between electrodes. Electrodes were energized with AC (alternating 10 Vpk-pk or ground along the electrode sequence) at specific frequencies. The well was placed on a microscope stage and light from the microscope passing through the well documents the position of cells within the well as cells are either attracted to the electrodes along the walls of the well (positive DEP) or repelled from the walls and collect at the center (negative DEP). The magnitude of the corresponding change in light absorbance across the well due to the local concentration of cells in the column is mathematically related to the polarisability of the cell population. The radial nature of the system means that there is a direct correlation between change in light intensity from a uniformly dispersed case as the field is applied and the value of polarisability of the cells in the well.

The well was observed using a Nikon inverted microscope equipped with a 1.3 Mpixel video camera, and the change in light intensity across the well over time was determined using a MATLAB (The Mathworks Inc, Natick, Mass.) script. The change in cell distribution was monitored by recording an image every 3 s for a total of 60 s and 21 images. The well was energized with frequencies ranging from 1 kHz-20 MHz at 5 points per decade. The analysis was focused on these frequencies to determine the dielectric properties of the membrane compartment of the cells since cytoplasmic contributions to the DEP response were at frequencies higher than 20 MHz (the outer limit of our function generator). Using MATLAB, light intensity measurements were fit to the single shell model (as in 24) and the best-fit model (minimum line correlation coefficient 0.98) was used to determine the specific membrane capacitance ($C_{spec}$), specific membrane conductance ($G_{spec}$), and crossover frequency (the frequency where the DEP force is zero). For DEP electrophysiology calculations, cell diameters and the diameter distribution were measured using the Cellometer Auto T4 cell counter (Nexcelom Bioscience, Lawrence, Mass.).

Statistical Analysis

Statistical analyses used Student's t test, and p-value<0.05 was considered significant. All data are expressed as means±SE of at least three independent experiments.

Results

Figure 4A:
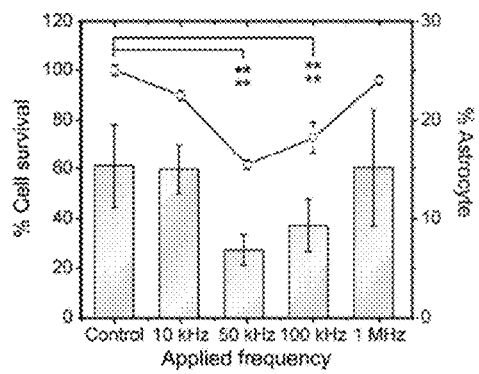
FIG. 4A illustrates a graph of applied frequency to the DEP electrodes showing cell survival percentage (left side) and astrocyte percentage (right side).

It was first tested whether exposure to DEP frequencies altered the differentiation of huNSPCs (SC23) by exposing the cells to various frequencies for 30 min and inducing differentiation afterward by changing the substrate and medium composition. NSPCs isolated from central nervous system normally generate three cell types: neurons, astrocytes, and oligodendrocytes. The generation of neurons and astrocytes are measured here, but not oligodendrocytes because special hypoxic conditions are required to generate these cells from huNSPCs in vitro. No significant change in neuronal lineage production was noticed even with significant cell destruction at 50 kHz. Cell survival is shown in FIG. 4A (left axis). Data is not shown for the production of neurons. It was suspected that because huNSPCs (SC23) only produced less than 0.2% neurons in culture, it is hard to detect the changes in neuron production for this specific set of huNSPCs. However, a direct correlation was found between the amount of cells being damaged by DEP exposure and the production of astrocytes (GFAP+/Sox2−) (FIG. 4A), which implied that DEP exposure either changed the fate of stem cells at specific frequency, such as 50 kHz or 100 kHz, or selectively damaged astrocytic progenitors in the culture. DEP exposure at 50 kHz selectively damages astrocytic progenitors in the culture.

Figure 4B:
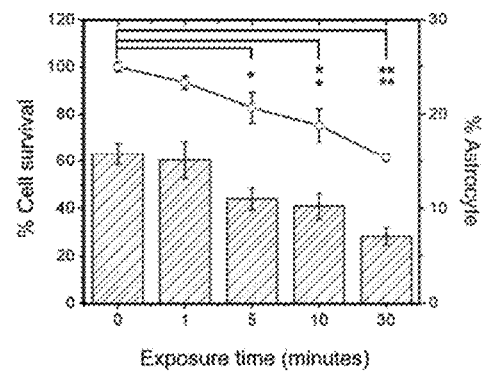
FIG. 4B illustrates a graph of exposure time (minutes) for the DEP electrodes showing cell survival percentage (left side) and astrocyte percentage (right side).

It was assessed whether the production of astrocytes linked strongly to the DEP induced cell destruction by exposing cells to 50 kHz with distinct exposure duration, 1, 5, 10, and 30 min. Interestingly, the longer the huNSPCs exposed to DEP force at 50 kHz, the more the cells were damaged, and the fewer astrocytes were produced (FIG. 4B). This result suggested that DEP induced cell destruction of huNSPCs at 50 kHz and 100 kHz is associated with the reduction in astrocytic potential of huNSPCs (SC23).

Figure 5A:
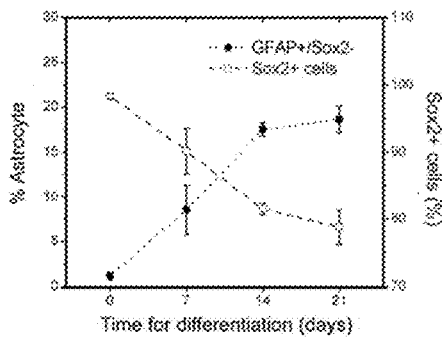
FIG. 5A illustrates a graph of astrocyte % (left side) and Sox2+ cells % (right side) as a function of time for differentiation. Percentage of astrocyte (GFAP+/Sox2− cells) production increased as cells differentiated for 0, 7, 14, and 21 days (1.2±0.5%, 8.5±2.8%, 17.5±0.7%, and 18.6±1.5%, respectively), while the percentage of Sox2+ cell decreased (98.3±0.5%, 90.1±3.4%, 81.5±0.8%, and 78.7±2.5%, respectively). The astrocyte production reached a plateau after 14 days of differentiation.
Figure 5B:
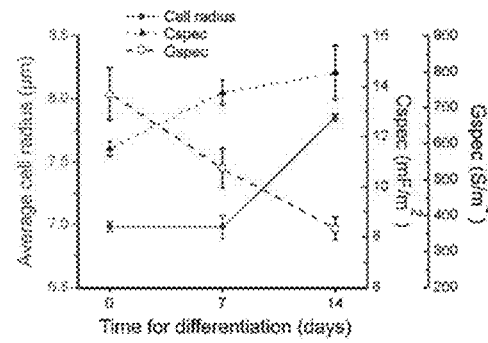
FIG. 5B illustrates a graph of average cell radius, $C_{spec}$, and $G_{spec}$ as a function of time for differentiation. The value for the membrane capacitance of the population increases as more astrocytes are produced in the populations.

The change in electrophysiological properties of huNSPCs (SC23) was measured during the astrocytic lineage induction. The amount of astrocyte production was measured over the period of 21 days in differentiation medium as well as their electrophysiological properties. An up-regulation in GFAP expression and down-regulation in Sox2 expression were found. When huNSPCs differentiated into astrocytic lineages, the amount of huNSPCs (Sox2+) reduced from 98.3±0.5% to 81.5±0.8% while the percentage of astrocytes in the culture increased, which reached its plateau at ~ day 14 (up to 17.5±0.7%, FIG. 5A). The electrophysiological properties of cells were measured using the DEP system and found an increase in $C_{spec}$ and decrease in $G_{spec}$ accompanied the astrocytic induction (FIG. 5B).

Figure 5C:
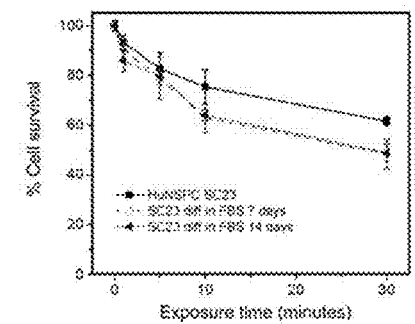
FIG. 5C illustrates cell survival of huNSPCs SC23, huNSPCs differentiated for 7 days, and huNSPCs differentiated for 14 days all decreased when exposed to DEP force at 50 kHz. Data are represented as mean±SE. (*, p-value<0.05 and **, p-value<0.01).

To further elucidate whether DEP exposure damaged either astrocytes or astrocytic progenitors in the huNSPCs culture, the sensitivity of cells at distinct stages of differentiation to DEP exposure at 50 kHz was measured. More cells were found to be damaged by DEP at 50 kHz for 30 min if there were more astrocytes existing in the culture. Interestingly, it was noted that a similar amount of cells were destroyed for huNSPCs (SC23) differentiated for both 7 and 14 days, suggesting that both astrocytes and astrocytic progenitors in the culture are more vulnerable to DEP exposure at 50 kHz compared to undifferentiated huNSPCs (FIG. 5C).

To determine the key factors contributing to the DEP induced cell destruction, cell size distribution and population-level electrophysiological properties were analyzed prior to and post-DEP exposure at 50 kHz and 1 MHz for 30 minutes. Exposing cells to 1 MHz was used as a control to clarify if AC electric field exposure would change cellular biophysical characteristics, such as cell size and electrophysiological properties. No significant changes in cell size or electrophysiological properties, specific to membrane capacitance and conductance, were detected between control (no DEP exposure) cells and cells exposed to 1 MHz up to 30 min as seen in FIG. 6A and FIG. 6B. This suggested the biophysical characteristics of cells would not be altered by AC electric field exposure energized by 8 V peak-peak. No changes in cell size was detected before and after DEP induced cell destruction at 50 kHz, implying cell-size independent cell destruction during the DEP exposure (FIG. 6A). Notably, a significant change in the population-level electrophysiological properties between cells without DEP exposure and cells post-DEP destruction was identified seen in FIG. 6C. A significant lower value, approximately 30% less than the value derived from the control, for membrane capacitance was identified for the huNSPCs not damaged by DEP exposure at 50 kHz. Because AC electric field exposure could not alter the electrophysiological properties of cells, this finding confirmed that a subpopulation of huNSPCs with high membrane capacitance in the culture was destroyed by DEP. Because the huNSPCs with higher astrocytic potential has been found to have higher membrane capacitance, this result suggested that applying DEP force at 50 kHz to huNSPCs (SC23) selectively destroy astrocytic progenitors in the culture.

While embodiments of the present invention have been shown and described, various modifications may be made without departing from the scope of the present invention. The invention, therefore, should not be limited, except to the following claims, and their equivalents.

What is claimed is:

1. A method for enriching a heterogeneous population of stem cells comprising:
   loading one or more sample chambers containing DEP electrodes therein with a solution containing the heterogeneous population of stem cells, wherein the heterogeneous population of stem cells comprises a first subpopulation of stem cells having a first crossover frequency and a second subpopulation of stem cells having a second, higher crossover frequency; and
   applying an AC electrical field to the DEP electrodes, wherein the AC electrical field has an applied frequency that is just above the crossover frequency of the first subpopulation of stem cells and below the second subpopulation of stem cells, wherein the first subpopulation of stem cells are substantially killed by the applied electrical field and the second subpopulation of stem cells are substantially not killed by the applied electrical field.

2. The method of claim 1, wherein the one or more sample chambers comprise wells, wherein the DEP electrodes are disposed at the bottom of the respective wells.

3. The method of claim 2, wherein the one or more wells have a depth of at least 150 µm.

4. The method of claim 1, further comprising collecting the samples from the one or more sample chambers and subjecting the same to centrifugation.

5. The method of claim 1, wherein the heterogeneous population of stem cells comprises one or more of astrocytic progenitors, Neural Stem Precursor Cells (NSPCs), and neuronal progenitors.

6. The method of claim 1, wherein the applied AC electrical field has a peak-to-peak voltage of at least 8V.

7. The method of claim 1, wherein the applied AC electrical field is applied for at least 10 seconds.

8. The method of claim 1, wherein the applied AC electrical field is applied for at least 30 seconds.

9. The method of claim 1, wherein the applied AC electrical field is applied between 5 and 30 minutes.

10. The method of claim 1, wherein the applied AC electrical field is applied between 1 and 4 minutes.

11. The method of claim 1, further comprising removing a portion of the solution contained in the one or more sample chambers.

12. The method of claim 11, further subjecting the removed portion of the solution to centrifugation.

13. The method of claim 1, wherein the AC electrical field has an applied frequency of around 50 kHz.

14. The method of claim 13, wherein the heterogeneous population of cells comprises Neural Stem Precursor Cells (NSPCs) and astrocytic progenitors, and wherein the astrocytic progenitors are substantially killed by the applied electrical field.

15. A method for enriching a heterogeneous population of cancer cells and healthy cells comprising:
   loading one or more sample chambers containing DEP electrodes therein with a solution containing the heterogeneous population of cancer cells and healthy cells, wherein the heterogeneous population of cancer cells and healthy cells comprises a first subpopulation of cancer cells having a first crossover frequency and a second subpopulation of healthy cells having a second, higher crossover frequency; and
   applying an AC electrical field to the DEP electrodes, wherein the AC electrical field has an applied frequency that is just above the crossover frequency of the first subpopulation of cancer cells and below the second subpopulation of healthy cells, wherein the first subpopulation of cancer cells are substantially killed by the applied electrical field and the second subpopulation of healthy cells are substantially not killed by the applied electrical field.

* * * * *